(12) United States Patent
Shaffer

(10) Patent No.: US 10,857,375 B2
(45) Date of Patent: **\*Dec. 8, 2020**

(54) TREATMENT SPINAL CORD INJURIES VIA LASER THERAPY

(71) Applicant: Steven E. Shaffer, Costa Mesa, CA (US)

(72) Inventor: Steven E. Shaffer, Costa Mesa, CA (US)

(73) Assignee: Luberski Inc., Fullerton, CA (US)

( \* ) Notice: Subject to any disclaimer, the term of this patent is extended or adjusted under 35 U.S.C. 154(b) by 124 days.

This patent is subject to a terminal disclaimer.

(21) Appl. No.: 16/127,057

(22) Filed: Sep. 10, 2018

(65) Prior Publication Data

US 2019/0001147 A1    Jan. 3, 2019

Related U.S. Application Data

(63) Continuation of application No. 14/077,053, filed on Nov. 11, 2013, now Pat. No. 10,071,260, which is a continuation of application No. 13/367,277, filed on Feb. 6, 2012, now Pat. No. 8,728,135.

(51) Int. Cl.
| | |
|---|---|
| *A61N 5/06* | (2006.01) |
| *A61H 1/00* | (2006.01) |
| *A61B 18/00* | (2006.01) |
| *A61N 5/067* | (2006.01) |
| *A61H 23/00* | (2006.01) |
| *A61H 39/00* | (2006.01) |

(52) U.S. Cl.
CPC .............. *A61N 5/06* (2013.01); *A61H 1/00* (2013.01); *A61N 5/0622* (2013.01); *A61B 2018/00339* (2013.01); *A61H 23/00* (2013.01); *A61H 2039/005* (2013.01); *A61H 2201/10* (2013.01); *A61H 2201/5007* (2013.01); *A61H 2201/5012* (2013.01); *A61H 2205/081* (2013.01); *A61N 2005/067* (2013.01)

(58) Field of Classification Search
CPC ........................................................ A61N 5/06
USPC ..................................... 606/2–19; 607/88–94
See application file for complete search history.

(56) References Cited

U.S. PATENT DOCUMENTS

| | | |
|---|---|---|
| 6,063,108 A | 5/2000 | Salansky et al. |
| 6,273,905 B1 | 8/2001 | Streeter |
| 2007/0208289 A1 | 9/2007 | Walther et al. |

*Primary Examiner* — Lynsey C Eiseman
(74) *Attorney, Agent, or Firm* — Sherrie Flynn; Coleman & Horowitt LLP

(57) ABSTRACT

Aspects for treating spinal cord injuries are disclosed. In a particular aspect, a method includes identifying a neurological level of a spinal cord injury, and activating neurons via laser therapy in which a laser beam is applied to an area proximate to the neurological level. In another aspect, a computer-readable storage medium includes computer-readable instructions for performing various acts. Such acts comprise ascertaining a neurological level of a spinal cord injury, and receiving data corresponding to a severity of the spinal cord injury. The acts further comprise outputting a laser calibration according to the neurological level and the severity. A medical device apparatus is also provided, which includes various computer executable components. The computer executable components include an assessment component configured to receive parameters corresponding to a spinal cord injury, and a calibration component configured to ascertain a laser calibration according to the at least one parameter.

20 Claims, 9 Drawing Sheets

TREATMENT SPINAL CORD INJURIES VIA LASER THERAPY

CROSS-REFERENCE TO RELATED APPLICATIONS

This application is a continuation of U.S. patent application Ser. No. 14/077,053, filed Nov. 11, 2013 (U.S. Pat. No. 10,071,260 to be issued Sep. 11, 2018), which is a continuation of U.S. patent application Ser. No. 13/367,277, filed Feb. 6, 2012, now U.S. Pat. No. 8,728,135, both entitled "TREATING SPINAL CORD INJURIES VIA LASER THERAPY," which are incorporated herein by reference in their entireties.

TECHNICAL FIELD

The subject disclosure generally relates to a treatment for spinal cord injuries, and more specifically to treating spinal cord injuries via laser therapy.

BACKGROUND

By way of background concerning spinal cord injuries, it is noted that spinal cord injury patients often report an inability to feel their body as well as they had prior to their injury. Stimulating the regeneration of axons is often a goal of spinal cord repair since such regeneration increases the chances for recovering function. Namely, reconnecting any axon in the injured spinal cord increases the chances for recovery of function.

Research on many fronts, however, reveals that regenerating axons after injury is a complicated task. For instance, although neurons in the central nervous system (CNS) have the capacity to regenerate, the environment in the adult spinal cord does not encourage such growth. Not only does the spinal cord lack growth-promoting molecules present in the developing CNS, it also includes substances that actively inhibit axon extension. Indeed, the environment of the adult CNS is particularly hostile to axon growth because growth-inhibiting proteins are embedded in myelin, the insulating material around axons. It is believed that these proteins preserve neural circuits in healthy spinal cords and keep intact axons from growing inappropriately. But when the spinal cord is injured, these proteins prevent regeneration.

Accordingly, it would be desirable to provide a methodology for treating spinal cord injuries which overcomes these limitations. To this end, it should be noted that the above-described deficiencies are merely intended to provide an overview of some of the problems of conventional systems, and are not intended to be exhaustive. Other problems with the state of the art and corresponding benefits of some of the various non-limiting embodiments may become further apparent upon review of the following detailed description.

SUMMARY

A simplified summary is provided herein to help enable a basic or general understanding of various aspects of exemplary, non-limiting embodiments that follow in the more detailed description and the accompanying drawings. This summary is not intended, however, as an extensive or exhaustive overview. Instead, the sole purpose of this summary is to present some concepts related to some exemplary non-limiting embodiments in a simplified form as a prelude to the more detailed description of the various embodiments that follow.

In accordance with one or more embodiments and corresponding disclosure, various non-limiting aspects are described in connection with treating spinal cord injuries via laser therapy. In one such aspect, a method that facilitates treating spinal cord injuries is provided. The method includes identifying a neurological level of a spinal cord injury, and activating neurons via laser therapy. Within such embodiment, a laser beam is applied to an area proximate to the neurological level.

In another aspect, a computer-readable storage medium that facilitates treating spinal cord injuries is provided. For this embodiment, the computer-readable storage medium includes computer-readable instructions for causing at least one processor to perform various acts. Such acts comprise ascertaining a neurological level of a spinal cord injury, and receiving data corresponding to a severity of the spinal cord injury. The acts further comprise outputting a laser calibration according to the neurological level and the severity.

In yet another aspect, a medical device apparatus that facilitates treating spinal cord injuries is provided. Within such embodiment, the apparatus includes a processor configured to execute computer executable components stored in memory. The computer executable components include an assessment component, and a calibration component. The assessment component is configured to receive at least one parameter corresponding to a spinal cord injury, whereas the calibration component is configured to ascertain a laser calibration according to the at least one parameter.

Other embodiments and various non-limiting examples, scenarios and implementations are described in more detail below.

BRIEF DESCRIPTION OF THE DRAWINGS

Various non-limiting embodiments are further described with reference to the accompanying drawings in which.

DETAILED DESCRIPTION

Overview

As discussed in the background, it is desirable to effectively treat patients who have sustained spinal cord injuries. The various embodiments disclosed herein are directed towards treating spinal cord injuries with a laser therapy. For instance, a laser therapy is disclosed which enables a body to discover previously under-utilized nervous system pathways and accentuate their procedural participation. In another aspect, a laser therapy is disclosed which facilitates a development of new neuronal connections.

In a particular embodiment, spinal cord injury patients are provided with a custom laser therapy that varies according to the severity and/or location of the injury. To this end, it should be noted that customizing various parameters of the laser therapy disclosed herein have been discovered to be particularly effective. For instance, rather than generically applying a laser to the entire spinal cord, it has been discovered that healing is substantially expedited when a laser is applied onto the specific neurological level of the injury, wherein the calibration and application angle of the laser varies according to the severity of the injury. In a further aspect, it has been discovered that particularly desirable results are attained when the aforementioned laser therapy is coupled with simultaneous tactile stimulation of a dermatome corresponding to the neurological level of the injury.

Figure 1:
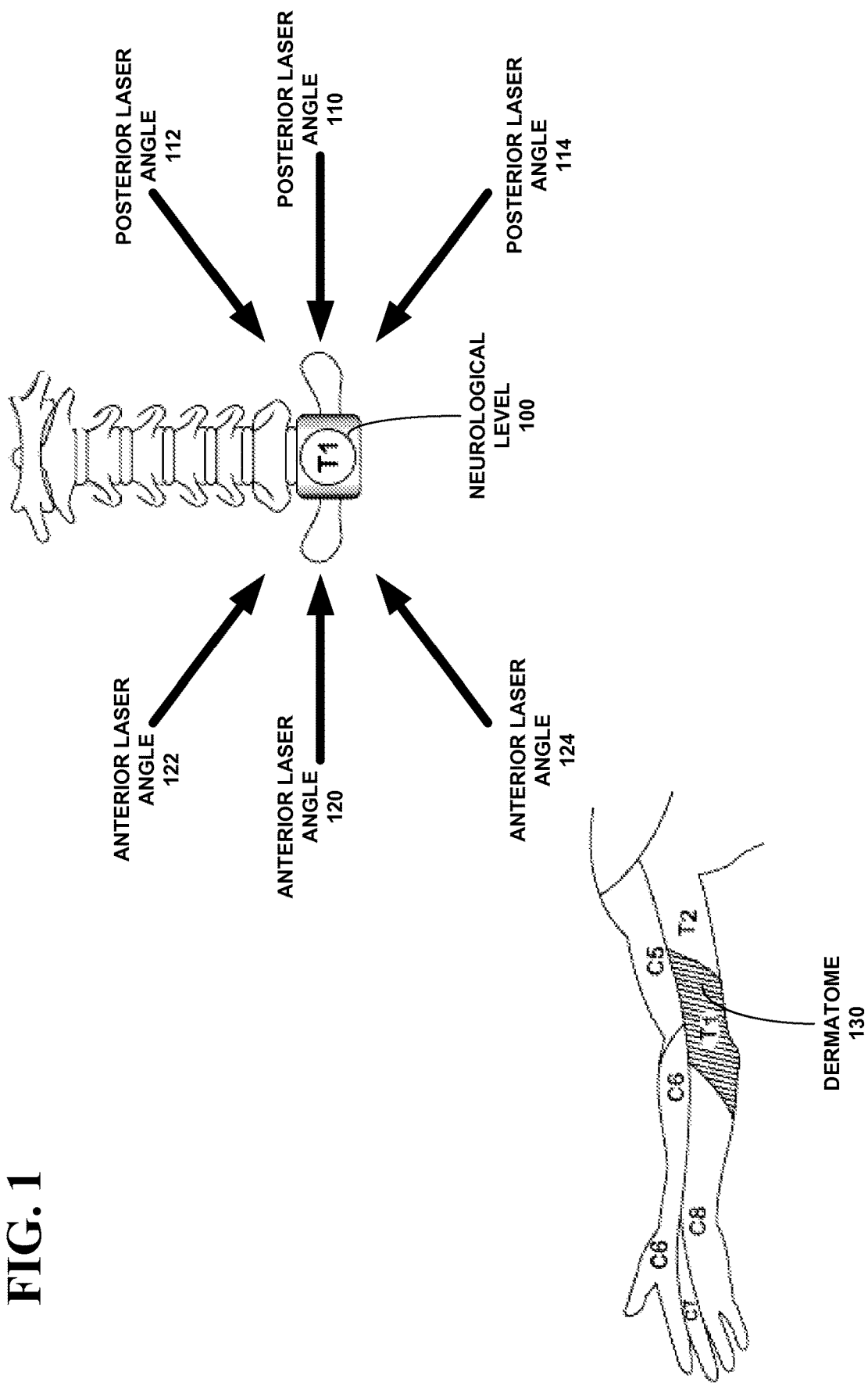
FIG. 1 illustrates an exemplary neurological level and corresponding dermatome according to an embodiment.

Turning now to FIG. 1, an exemplary neurological level and corresponding dermatome is provided according to an embodiment. As illustrated, it is contemplated that a laser can be applied to the neurological level of an injury via any of a plurality of angles. For this particular example, neurological level 100 is a T1 neurological level, wherein it is contemplated that a laser be applied to neurological level 100 via any combination of posterior angle 110, posterior angle 112, posterior angle 114, anterior angle 120, anterior angle 122, and/or anterior angle 124. To this end, it should be appreciated that the application angle of the laser may depend on any of various factors including, but not limited to, the desired neuron type to be activated. For instance, it has been discovered that motor-related neurons are particularly responsive when a laser is applied via an anterior angle, whereas sensory nerves are generally more responsive when applying a laser via a posterior angle. Furthermore, as illustrated, it is contemplated that it may sometimes be desirable to apply a laser via non-perpendicular angles, such as posterior angle 112, posterior angle 114, anterior angle 122, and/or anterior angle 124. Indeed, it is contemplated that varying between perpendicular and non-perpendicular angles can expose a wider range of neurons to the laser therapy, and thus increase total neuron activation.

In a further aspect, it has been discovered that other laser characteristics can be customized to yield optimal results as well. For instance, a laser can be calibrated according to a particular injury's severity to provide a customized laser treatment. Exemplary calibrations may include, but are not limited to, a pulsed frequency calibration, a power calibration, and/or a wavelength calibration. The width of the laser can also be varied, although a width between 800-970 nanometers has been discovered to be particularly effective.

As stated previously, some embodiments include simultaneously applying a laser onto the neurological level of the injury while stimulating a corresponding dermatome. In the example illustrated in FIG. 1, for instance, dermatome 130 corresponds to neurological level 100. Accordingly, within such embodiment, a laser is applied onto neurological level 100 concurrently with the tactile stimulation of dermatome 130. Exemplary tactile stimulations may include, but are not limited to, a pain stimulation, a vibration stimulation, a temperature stimulation, and/or a light touch stimulation.

Figure 2:
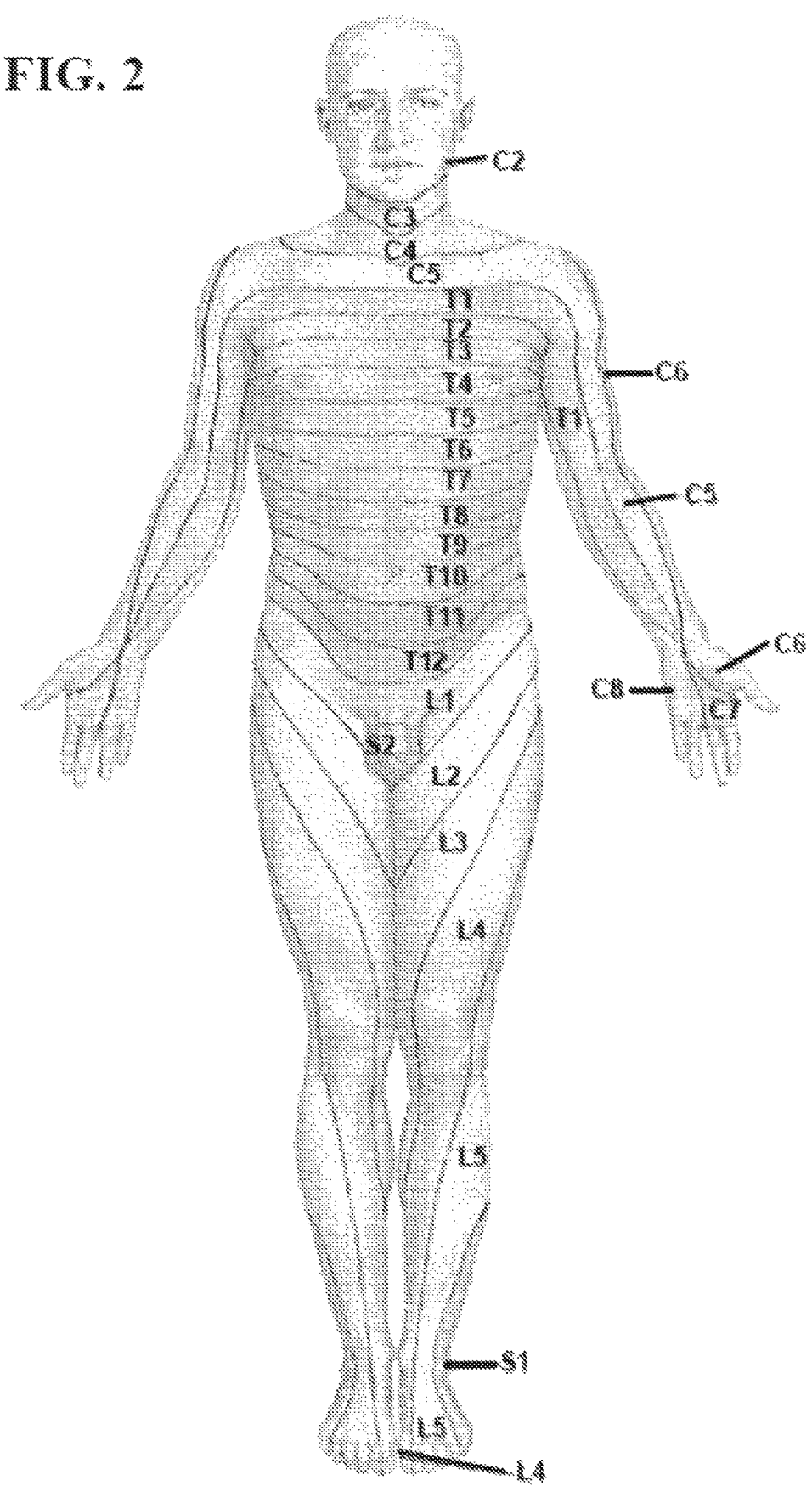
FIG. 2 illustrates an exemplary schematic demarcation of dermatomes in accordance with an aspect of the subject specification.
Figure 3:
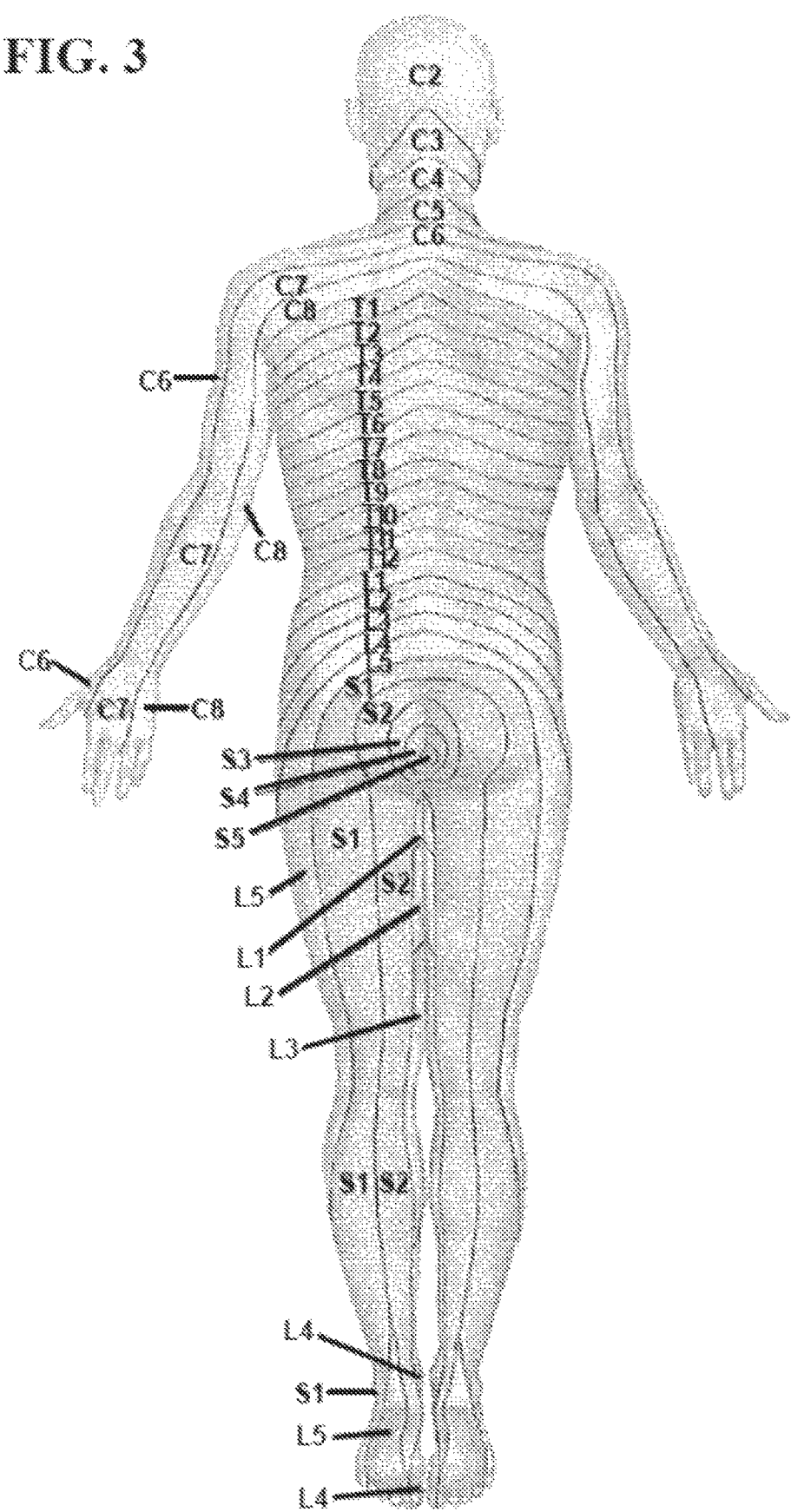
FIG. 3 illustrates another exemplary schematic demarcation of dermatomes in accordance with an aspect of the subject specification.

With respect to determining which dermatomes correspond to particular neurological levels, it is noted that any of various dermatome mapping diagrams can be used. For instance, FIG. 2 illustrates a front view of an exemplary schematic demarcation of dermatomes, whereas FIG. 3 illustrates a back view of an exemplary schematic demarcation of dermatomes. To this end, although the schematic demarcations in FIGS. 2-3 are shown as distinct segments, it should be appreciated that some overlap between adjacent dermatomes may exist.

Figure 4:
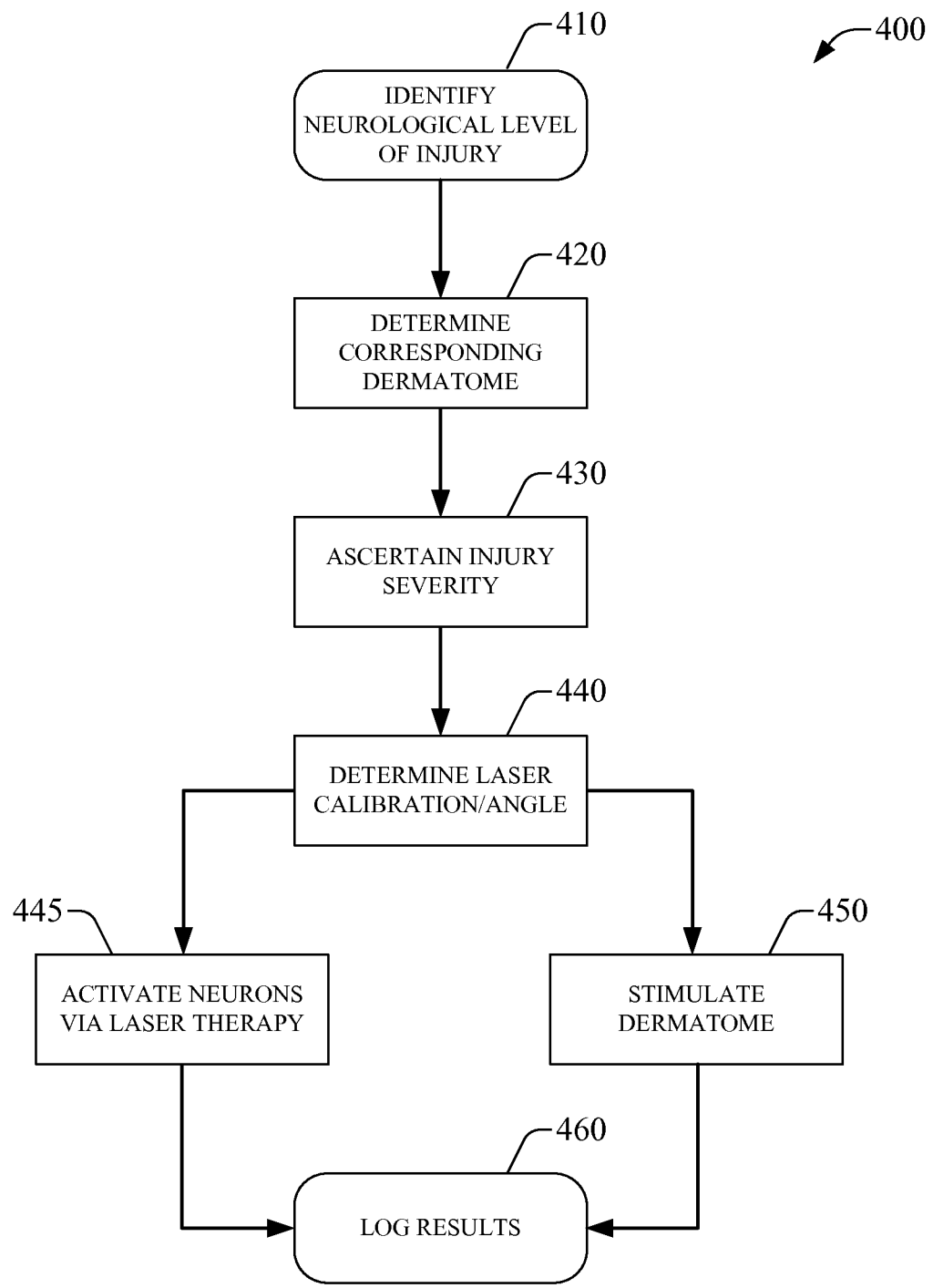
FIG. 4 illustrates a flow diagram of an exemplary methodology for treating spinal cord injuries in accordance with an aspect of the subject specification.

Referring next to FIG. 4, a flow chart illustrating an exemplary method that facilitates treating spinal cord injuries is provided. As illustrated, process 400 includes a series of acts that may be performed by any of various entities (e.g., a medical professional, computing device, etc.) according to an aspect of the subject specification. For instance, aspects of process 400 may be implemented by employing a processor to execute computer executable instructions stored on a computer readable storage medium to implement the series of acts. In another embodiment, a computer-readable storage medium comprising code for causing at least one computer to implement the acts of process 400 are contemplated.

In an aspect, process 400 begins with an identification of the neurological level of a spinal cord injury at act 410. A dermatome corresponding to the neurological level of the spinal cord injury is then determined at act 420. As stated previously, identifying such dermatome may be facilitated by any of various dermatome mapping diagrams. Accordingly, it is contemplated that act 420 may be facilitated by a manual and/or automated use of such diagrams.

After identifying the injury's corresponding dermatome, process 400 continues to act 430 where a severity of the injury is ascertained. In an aspect, an assessment of such severity may include a dermatome assessment of the injury. For instance, it is contemplated that any of a plurality of dermatome assessments may be performed including, for example, a pain assessment, a vibration assessment, a temperature assessment, and/or a light touch assessment.

Process 400 then proceeds to act 440 where a laser calibration/angle is determined. As stated previously, exemplary calibrations may include, but are not limited to, a pulsed frequency calibration, a power calibration, and/or a wavelength calibration, whereas exemplary angles may include any of a plurality of angles from which to apply a laser (e.g., via a perpendicular/non-perpendicular posterior angle, a perpendicular/non-perpendicular anterior angle, etc.). In an exemplary embodiment, since determining the appropriate laser calibration/angle for treating a particular injury may vary according to the severity and/or neurological location of the injury, act 440 may be facilitated by referencing a lookup table. For example, such lookup table may be an electronic lookup table, wherein data regarding the severity and/or neurological location of an injury is provided as an input, and wherein an appropriate laser calibration/angle corresponding to the severity and/or neurological location of the injury is output.

Once the appropriate laser calibration/angle is determined, a patient can be treated according to the aspects disclosed herein. For this particular example, process 400 proceeds by simultaneously activating neurons via laser therapy at act 445 and stimulating a corresponding dermatome at act 450. Namely, it is contemplated that act 445 comprises applying a laser onto the neurological location of the injury according to the laser calibration/angle determined at act 440, whereas act 450 comprises stimulating a corresponding dermatome (e.g., via a pain stimulation, a vibration stimulation, a temperature stimulation, a light touch stimulation, etc.) concurrently with the application of the laser. Process 400 then concludes at act 460 where results corresponding to the patient's progress are logged manually and/or electronically.

Figure 5:
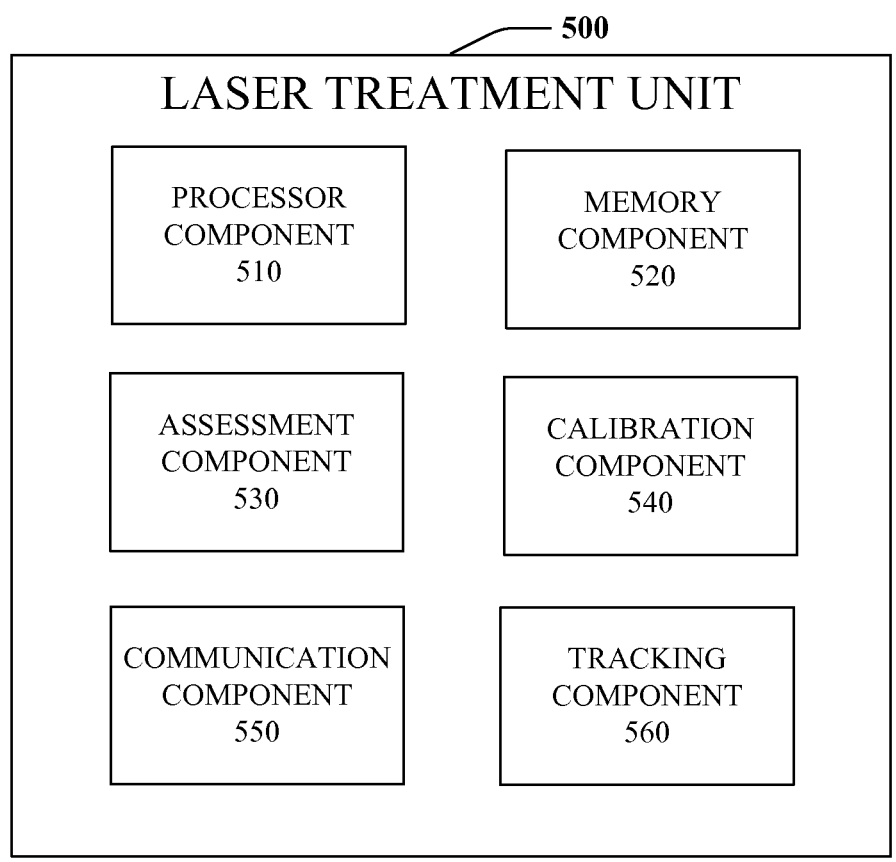
FIG. 5 illustrates a block diagram of an exemplary laser treatment unit that facilitates treating spinal cord injuries in accordance with an aspect of the subject specification.

Referring next to FIG. 5, an exemplary laser treatment unit that facilitates treating spinal cord injuries according to an embodiment is illustrated. As shown, laser treatment unit 500 may include processor component 510, memory component 520, assessment component 530, calibration component 540, communication component 550, and tracking component 560. Here, it should be noted that processor component 510, memory component 520, assessment component 530, calibration component 540, communication component 550, and/or tracking component 560 can reside together in a single location or separated in different locations in various combinations.

In one aspect, processor component 510 is configured to execute computer-readable instructions related to performing any of a plurality of functions. Processor component 510 can be a single processor or a plurality of processors which analyze and/or generate information utilized by memory component 520, assessment component 530, calibration component 540, communication component 550, and/or tracking component 560. Additionally or alternatively, processor component 510 may be configured to control one or more components of laser treatment unit 500.

In another aspect, memory component 520 is coupled to processor component 510 and configured to store computer-readable instructions executed by processor component 510. Memory component 520 may also be configured to store any of a plurality of other types of data including data generated by any of assessment component 530, calibration component 540, communication component 550, and/or tracking component 560. Memory component 520 can be configured in a number of different configurations, including as random access memory, battery-backed memory, hard disk, magnetic tape, etc. Various features can also be implemented upon memory component 520, such as compression and automatic back up (e.g., use of a Redundant Array of Independent Drives configuration).

As illustrated, laser treatment unit 500 may also include assessment component 530, which is configured to receive any of a plurality of parameters corresponding to a spinal cord injury. For instance, in a particular embodiment, at least one parameter corresponds to a neurological level of the spinal cord injury. However, it is also contemplated that at least one parameter corresponds to a severity of the spinal cord injury. Within such embodiment, the severity may include a dermatome assessment of the spinal cord injury, for example.

In another aspect, laser treatment unit 500 also includes calibration component 540. Here, it is contemplated that calibration component 540 is configured to ascertain a laser calibration according to the parameter(s) received via assessment component 530. To this end, it should be noted that calibration component 540 can be configured to provide any of a plurality of laser calibrations including, for example, a pulsed frequency calibration, a power calibration, and/or a wavelength calibration. Also, with respect to ascertaining such calibrations, it should be noted that calibration component 540 may be configured to ascertain laser calibrations in any of a plurality of ways. For instance, calibration component 540 may be configured to retrieve laser calibrations from a look up table according to the parameter(s) received via assessment component 530.

As illustrated, laser treatment unit 500 may also include communication component 550 and tracking component 560. Within such embodiment, communication component 550 is configured to interface laser treatment unit 500 with external entities, whereas tracking component 560 is configured to log a laser treatment history associated with laser treatment unit 500. Moreover, it is contemplated that communication component 550 may be configured to receive and/or transmit any of various types of data according to any of a plurality of communication protocols, and that tracking component 560 may be configured to log various types of data associated with a laser therapy (e.g., laser calibration history, patient progress, etc.).

Figure 6:
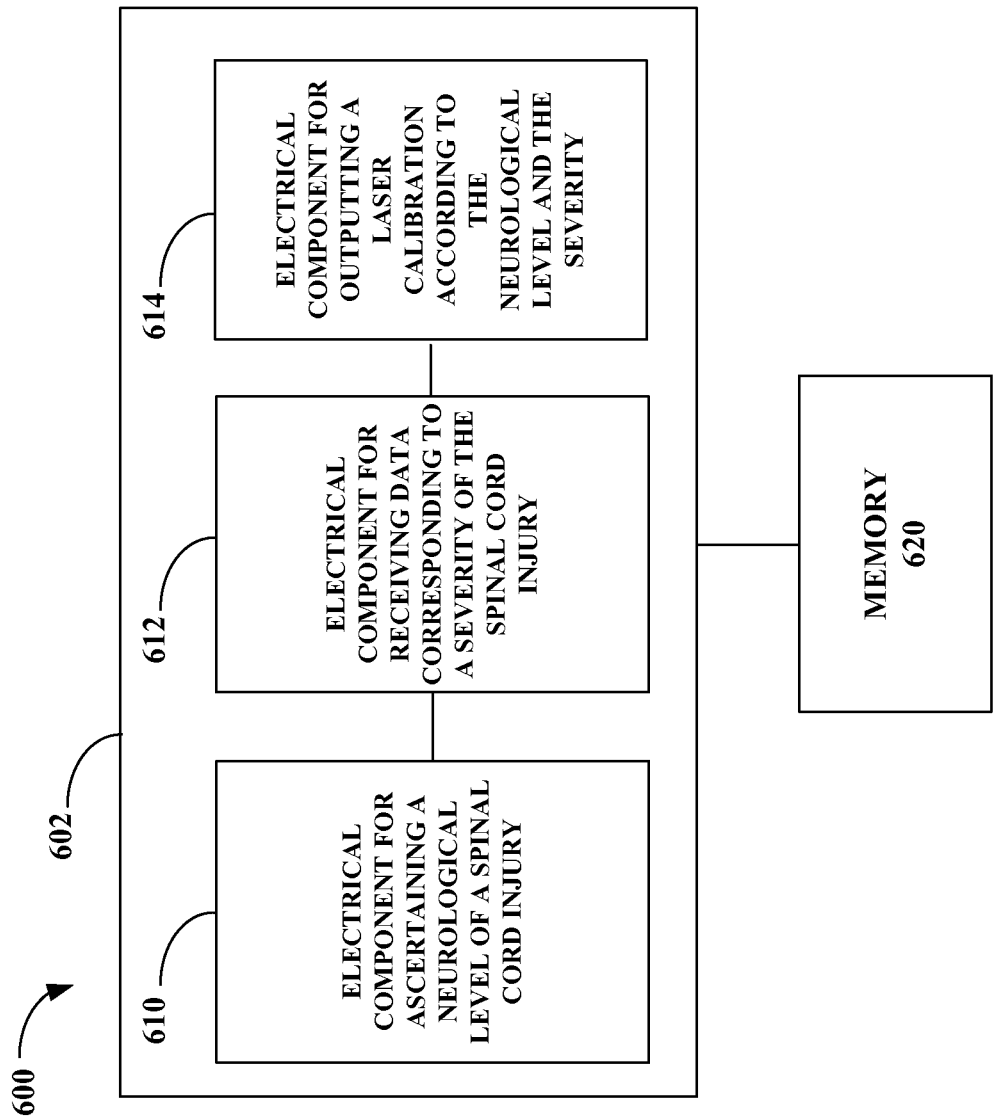
FIG. 6 illustrates an exemplary coupling of electrical components that effectuate treating spinal cord injuries according to an embodiment.

Referring next to FIG. 6, illustrated is an exemplary system 600 that facilitates treating spinal cord injuries according to an embodiment. System 600 and/or instructions for implementing system 600 can reside within a computing device, for example. As depicted, system 600 includes functional blocks that can represent functions implemented by a processor using instructions and/or data from a computer readable storage medium. System 600 includes a logical grouping 602 of electrical components that can act in conjunction. As illustrated, logical grouping 602 can include an electrical component for ascertaining a neurological level of a spinal cord injury 610. Furthermore, logical grouping 602 can include an electrical component for receiving data corresponding to a severity of the spinal cord injury 612. Logical grouping 602 can also include an electrical component for outputting a laser calibration according to the neurological level and the severity 614. As illustrated, system 600 can include a memory 620 configured to retain instructions for executing functions associated with electrical components 610, 612, and 614. While shown as being external to memory 620, it should be appreciated that electrical components 610, 612, and 614 can exist within memory 620.

Figure 7:
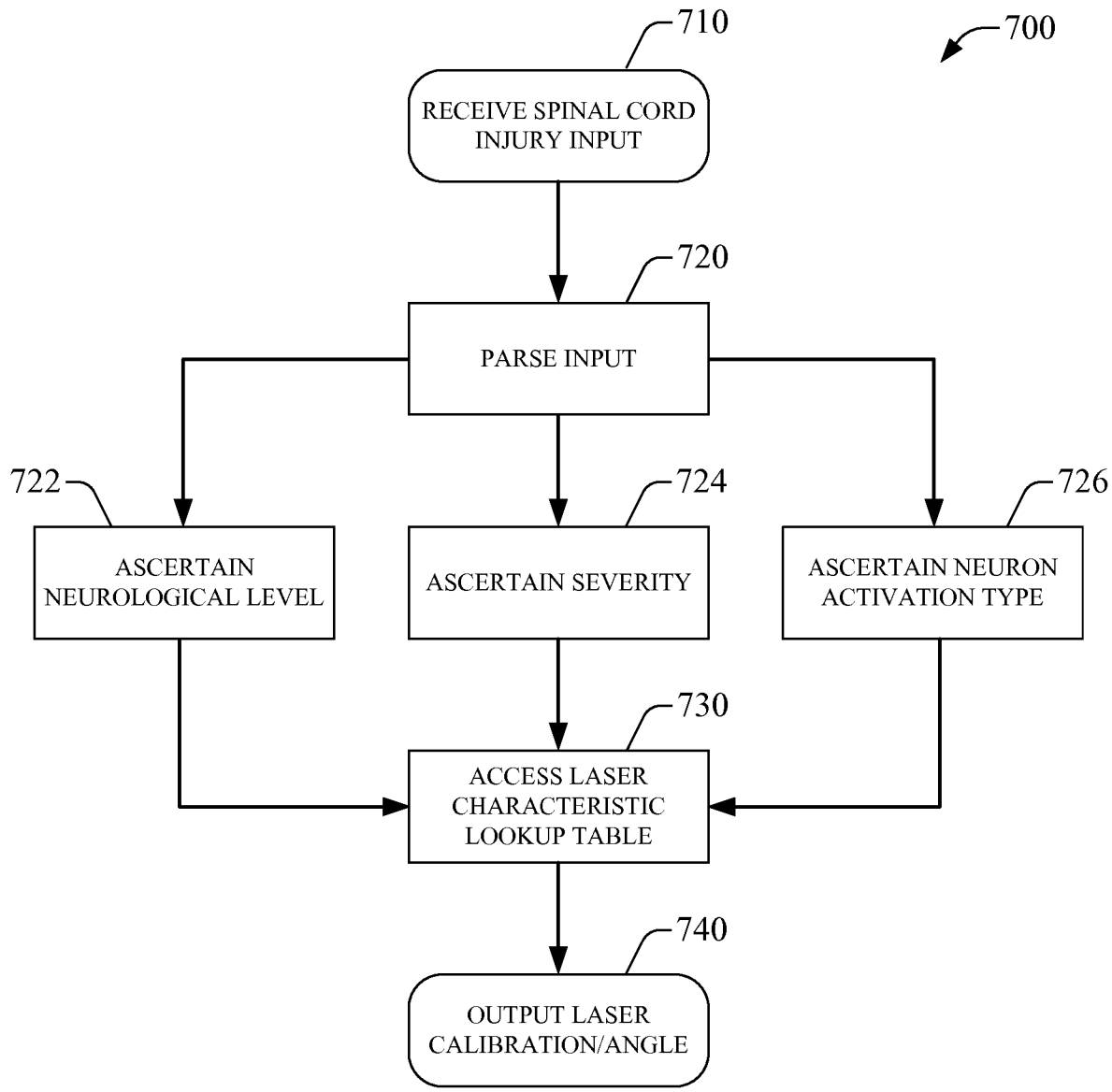
FIG. 7 illustrates a flow diagram of an exemplary methodology for automating a laser treatment for spinal cord injuries in accordance with an aspect of the subject specification.

Referring next to FIG. 7, a flow chart illustrating an exemplary method that facilitates automating a laser treatment for spinal cord injuries is provided. As illustrated, process 700 includes a series of acts that may be performed by any of various entities (e.g., laser treatment unit 500) according to an aspect of the subject specification. For instance, aspects of process 700 may be implemented by employing a processor to execute computer executable instructions stored on a computer readable storage medium to implement the series of acts. In another embodiment, a computer-readable storage medium comprising code for causing at least one computer to implement the acts of process 700 are contemplated.

In an aspect, process 700 begins with a spinal cord injury input being received at act 710. Here, as stated previously, it is contemplated that such input may include and/or identify various aspects associated with the injury. For instance, such input may include and/or identify various assessments entered by a medical professional including, for example, an assessment of the injury's neurological level (e.g., T1, L2, S1, etc.), severity (e.g., as determined by testing a corresponding dermatome via a pain assessment, vibration assessment, temperature assessment, light touch assessment, etc.), neuron activation type (e.g., motor-related neurons, sensory nerves, etc.), etc.

Accordingly, after receiving the input at act 710, process 700 proceeds with a parsing of the input at act 720 to ascertain the various aspects associated with the injury. For this particular example, the input is parsed, wherein a neurological level is ascertained at act 722, a severity is ascertained at act 724, and a neuron activation type is ascertained at act 726. From any combination of these parameters, it is then contemplated that a corresponding laser calibration/angle for optimally treating the injury. Namely, for this particular example, it is contemplated that a laser characteristic lookup table is accessed at act 730 to ascertain an optimal laser calibration/angle for treating the injury, wherein such calibration/angle is determined according to any combination of the particular injury-related aspects ascertained at acts 722, 724, and/or 726. Process 700 then concludes with the laser calibration/angle being output at act 740.

Exemplary Networked and Distributed Environments

One of ordinary skill in the art can appreciate that various embodiments for implementing the use of a computing device and related embodiments described herein can be implemented in connection with any computer or other client or server device, which can be deployed as part of a computer network or in a distributed computing environment, and can be connected to any kind of data store. Moreover, one of ordinary skill in the art will appreciate that such embodiments can be implemented in any computer system or environment having any number of memory or storage units, and any number of applications and processes occurring across any number of storage units. This includes, but is not limited to, an environment with server computers and client computers deployed in a network environment or a distributed computing environment, having remote or local storage.

Figure 8:
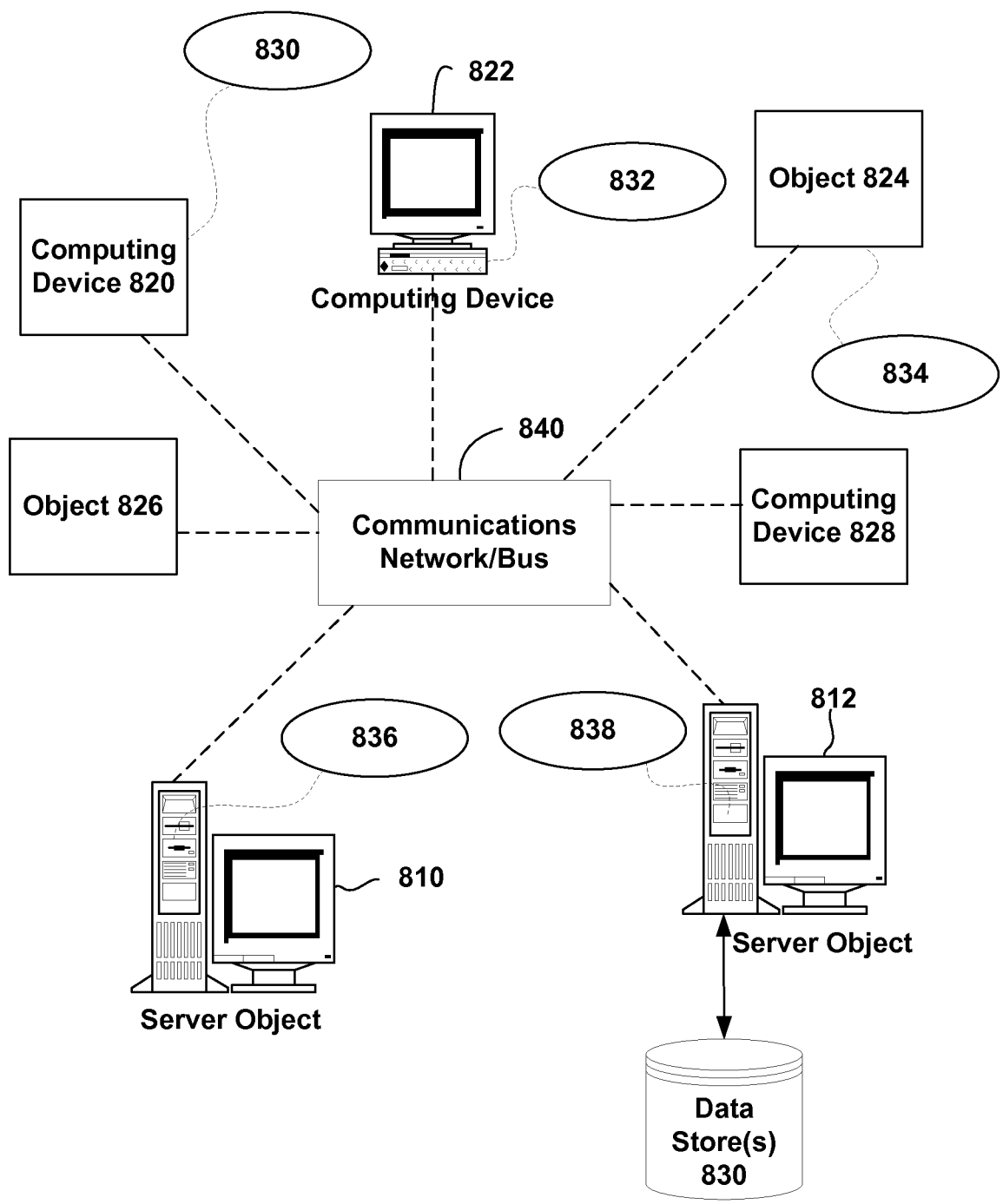
FIG. 8 is a block diagram representing exemplary non-limiting networked environments in which various embodiments described herein can be implemented.

FIG. 8 provides a non-limiting schematic diagram of an exemplary networked or distributed computing environment. The distributed computing environment comprises computing objects or devices 810, 812, etc. and computing objects or devices 820, 822, 824, 826, 828, etc., which may include programs, methods, data stores, programmable logic, etc., as represented by applications 830, 832, 834, 836, 838. It can be appreciated that computing objects or devices 810, 812, etc. and computing objects or devices 820, 822, 824, 826, 828, etc. may comprise different devices, such as PDAs (personal digital assistants), audio/video devices, mobile phones, MP3 players, laptops, etc.

Each computing object or device 810, 812, etc. and computing objects or devices 820, 822, 824, 826, 828, etc. can communicate with one or more other computing objects or devices 810, 812, etc. and computing objects or devices 820, 822, 824, 826, 828, etc. by way of the communications network 840, either directly or indirectly. Even though illustrated as a single element in FIG. 8, network 840 may comprise other computing objects and computing devices that provide services to the system of FIG. 8, and/or may represent multiple interconnected networks, which are not shown. Each computing object or device 810, 812, etc. or 820, 822, 824, 826, 828, etc. can also contain an application, such as applications 830, 832, 834, 836, 838, that might make use of an API (application programming interface), or other object, software, firmware and/or hardware, suitable for communication with or implementation of an infrastructure for information as a service from any platform as provided in accordance with various embodiments.

There are a variety of systems, components, and network configurations that support distributed computing environments. For example, computing systems can be connected together by wired or wireless systems, by local networks or widely distributed networks. Currently, many networks are coupled to the Internet, which provides an infrastructure for widely distributed computing and encompasses many different networks, though any network infrastructure can be used for exemplary communications made incident to the techniques as described in various embodiments.

Thus, a host of network topologies and network infrastructures, such as client/server, peer-to-peer, or hybrid architectures, can be utilized. In a client/server architecture, particularly a networked system, a client is usually a computer that accesses shared network resources provided by another computer, e.g., a server. In the illustration of FIG. 8, as a non-limiting example, computing objects or devices 820, 822, 824, 826, 828, etc. can be thought of as clients and computing objects or devices 810, 812, etc. can be thought of as servers where computing objects or devices 810, 812, etc. provide data services, such as receiving data from computing objects or devices 820, 822, 824, 826, 828, etc., storing of data, processing of data, transmitting data to computing objects or devices 820, 822, 824, 826, 828, etc., although any computer can be considered a client, a server, or both, depending on the circumstances. Any of these computing devices may be processing data, or requesting services or tasks that may facilitate treating spinal cord injuries via laser therapy and related techniques as described herein for one or more embodiments.

A server is typically a remote computer system accessible over a remote or local network, such as the Internet or wireless network infrastructures. The client process may be active in a first computer system, and the server process may be active in a second computer system, communicating with one another over a communications medium, thus providing distributed functionality and allowing multiple clients to take advantage of the information-gathering capabilities of the server. Any software objects utilized pursuant to the user profiling can be provided standalone, or distributed across multiple computing devices or objects.

In a network environment in which the communications network/bus 840 is the Internet, for example, the computing objects or devices 810, 812, etc. can be Web servers with which the computing objects or devices 820, 822, 824, 826, 828, etc. communicate via any of a number of known protocols, such as HTTP. As mentioned, computing objects or devices 810, 812, etc. may also serve as computing objects or devices 820, 822, 824, 826, 828, etc., or vice versa, as may be characteristic of a distributed computing environment.

Exemplary Computing Environment

As mentioned, several of the aforementioned embodiments apply to any device wherein it may be desirable to utilize a computing device to treat spinal cord injuries according to the aspects disclosed herein. It is understood, therefore, that handheld, portable and other computing devices and computing objects of all kinds are contemplated for use in connection with the various embodiments described herein, i.e., anywhere that a device may provide some functionality in connection with treating spinal cord injuries. Accordingly, the below general purpose remote computer described below in FIG. 9 is but one example, and the embodiments of the subject disclosure may be implemented with any client having network/bus interoperability and interaction.

Although not required, any of the embodiments can partly be implemented via an operating system, for use by a developer of services for a device or object, and/or included within application software that operates in connection with the operable component(s). Software may be described in the general context of computer executable instructions, such as program modules, being executed by one or more computers, such as client workstations, servers or other devices. Those skilled in the art will appreciate that network interactions may be practiced with a variety of computer system configurations and protocols.

Figure 9:
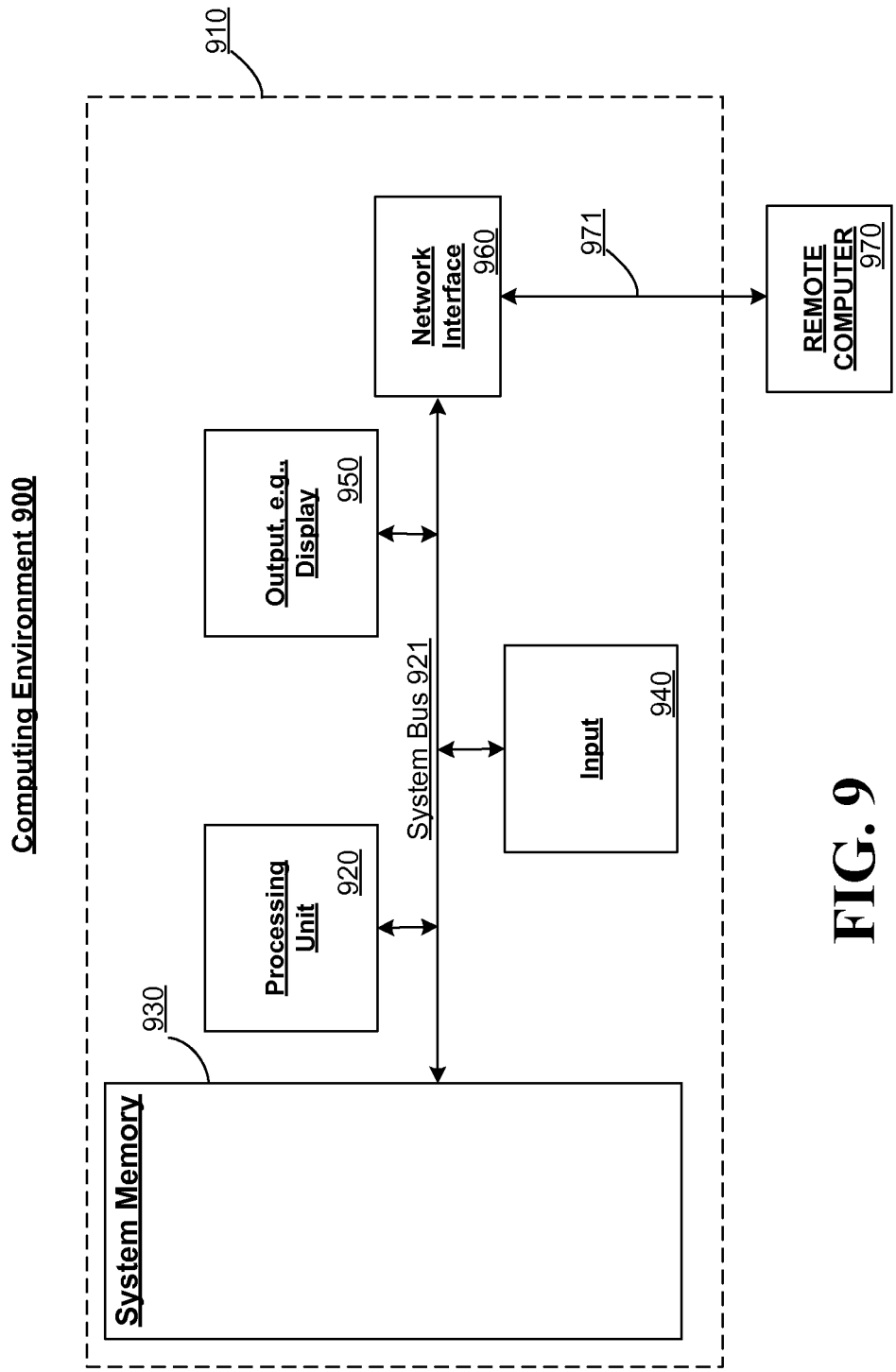
FIG. 9 is a block diagram representing an exemplary non-limiting computing system or operating environment in which one or more aspects of various embodiments described herein can be implemented.

FIG. 9 thus illustrates an example of a suitable computing system environment 900 in which one or more of the embodiments may be implemented, although as made clear above, the computing system environment 900 is only one example of a suitable computing environment and is not intended to suggest any limitation as to the scope of use or functionality of any of the embodiments. The computing environment 900 is not to be interpreted as having any dependency or requirement relating to any one or combination of components illustrated in the exemplary operating environment 900.

With reference to FIG. 9, an exemplary remote device for implementing one or more embodiments herein can include a general purpose computing device in the form of a handheld computer 910. Components of handheld computer 910 may include, but are not limited to, a processing unit 920, a system memory 930, and a system bus 921 that couples various system components including the system memory to the processing unit 920.

Computer 910 typically includes a variety of computer readable media and can be any available media that can be accessed by computer 910. The system memory 930 may include computer storage media in the form of volatile and/or nonvolatile memory such as read only memory (ROM) and/or random access memory (RAM). By way of example, and not limitation, memory 930 may also include an operating system, application programs, other program modules, and program data.

A user may enter commands and information into the computer 910 through input devices 940 A monitor or other type of display device is also connected to the system bus 921 via an interface, such as output interface 950. In addition to a monitor, computers may also include other peripheral output devices such as speakers and a printer, which may be connected through output interface 950.

The computer 910 may operate in a networked or distributed environment using logical connections to one or more other remote computers, such as remote computer 970. The remote computer 970 may be a personal computer, a server, a router, a network PC, a peer device or other common network node, or any other remote media consumption or transmission device, and may include any or all of the elements described above relative to the computer 910. The logical connections depicted in FIG. 9 include a network 971, such local area network (LAN) or a wide area network (WAN), but may also include other networks/buses. Such networking environments are commonplace in homes, offices, enterprise-wide computer networks, intranets and the Internet.

As mentioned above, while exemplary embodiments have been described in connection with various computing devices and networks, the underlying concepts may be applied to any network system and any computing device or system in which it is desirable to publish, build applications for or consume data in connection with treating spinal cord injuries.

There are multiple ways of implementing one or more of the embodiments described herein, e.g., an appropriate API, tool kit, driver code, operating system, control, standalone or downloadable software object, etc. which enables applications and services to facilitate treating spinal cord injuries via laser therapy. Embodiments may be contemplated from the standpoint of an API (or other software object), as well as from a software or hardware object that facilitates provision of an infrastructure for treating spinal cord injuries from any platform in accordance with one or more of the described embodiments. Various implementations and embodiments described herein may have aspects that are wholly in hardware, partly in hardware and partly in software, as well as in software.

The word "exemplary" is used herein to mean serving as an example, instance, or illustration. For the avoidance of doubt, the subject matter disclosed herein is not limited by such examples. In addition, any aspect or design described herein as "exemplary" is not necessarily to be construed as preferred or advantageous over other aspects or designs, nor is it meant to preclude equivalent exemplary structures and techniques known to those of ordinary skill in the art. Furthermore, to the extent that the terms "includes," "has," "contains," and other similar words are used in either the detailed description or the claims, for the avoidance of doubt, such terms are intended to be inclusive in a manner similar to the term "comprising" as an open transition word without precluding any additional or other elements.

As mentioned, the various techniques described herein may be implemented in connection with hardware or software or, where appropriate, with a combination of both. As used herein, the terms "component," "system" and the like are likewise intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on computer and the computer can be a component. One or more components may reside within a process and/or thread of execution and a component may be localized on one computer and/or distributed between two or more computers.

The aforementioned systems have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it is noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but generally known by those of skill in the art.

In view of the exemplary systems described supra, methodologies that may be implemented in accordance with the disclosed subject matter can be appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Where non-sequential, or branched, flow is illustrated via flowchart, it can be appreciated that various other branches, flow paths, and orders of the blocks, may be implemented which achieve the same or a similar result. Moreover, not all illustrated blocks may be required to implement the methodologies described hereinafter.

While in some embodiments, a client side perspective is illustrated, it is to be understood for the avoidance of doubt that a corresponding server perspective exists, or vice versa. Similarly, where a method is practiced, a corresponding device can be provided having storage and at least one processor configured to practice that method via one or more components.

While the various embodiments have been described in connection with the preferred embodiments of the various figures, it is to be understood that other similar embodiments may be used or modifications and additions may be made to the described embodiment for performing the same function without deviating there from. Still further, one or more aspects of the above described embodiments may be implemented in or across a plurality of processing chips or devices, and storage may similarly be affected across a plurality of devices. Therefore, the present invention should not be limited to any single embodiment, but rather should be construed in breadth and scope in accordance with the appended claims.

What is claimed is:

1. A medical device apparatus, comprising:
a laser configured to emit a laser beam;
a memory having computer executable instructions stored thereon; and a processor communicatively coupled to the memory, the processor executing the computer executable instructions to perform acts comprising:
receiving from a medical professional a neurological level of a patient's spinal cord injury and a neuron activation type;
calibrating the laser to activate neurons in an area proximate to the neurological level and at an application angle of the laser beam according to the neuron type to be activated; and
transmitting a communication to the medical professional to perform a deliberate tactile stimulation on a dermatome corresponding to the neurological level of the patient's spinal cord injury while activating the neuron type.

2. The medical device apparatus of claim 1, wherein the acts further comprise logging a laser treatment history associated with the patient.

3. The medical device apparatus of claim 1, wherein the acts further comprise tracking a laser calibration history associated with the patient.

4. The medical device apparatus of claim 1, wherein the acts further comprise tracking patient progress associated with the patient.

5. The medical device apparatus of claim 1, wherein the communication identifies a particular application angle of the laser, and wherein varying the particular application angle causes a desired neuron type to be activated more than a different neuron type.

6. The medical device apparatus of claim 5, wherein the particular application angle is an anterior angle when the desired neuron type is a motor neuron, and wherein the particular application angle is a posterior angle when the desired neuron type is a sensory neuron.

7. The medical device apparatus of claim 1, wherein the communication identifies a type of deliberate tactile stimulation, the type of deliberate tactile stimulation being at least one of a deliberate pain stimulation, a deliberate vibration stimulation, a deliberate temperature stimulation, or a deliberate light touch stimulation.

8. The medical device apparatus of claim 1, wherein the acts further comprise identifying a severity of spinal cord injury and calibrating the laser according to the severity of spinal cord injury.

9. A medical device apparatus, comprising:
a laser configured to emit a laser beam;
a memory having computer executable instructions stored thereon; and a processor communicatively coupled to the memory, the processor executing the computer executable instructions to perform acts comprising:
receiving from a medical professional a neurological level of a patient's spinal cord injury and a neuron activation type;
calibrating the laser to activate neurons in an area proximate to the neurological level and at one or more application angles of the laser beam according to the neuron type to be activated, wherein when the neuron type is motor neurons, the one or more application angles are anterior angles and when the neuron type is sensory neurons, the one or more application angles are posterior angles; and
transmitting a communication to the medical professional to perform a deliberate tactile stimulation on a dermatome corresponding to the neurological level of the patient's spinal cord injury while activating the neuron type.

10. The medical device apparatus of claim 9, wherein the deliberate tactile stimulation is one of a deliberate pain stimulation, a deliberate vibration stimulation, a deliberate temperature stimulation, or a deliberate light touch stimulation.

11. The medical device apparatus of claim 9, wherein the acts further comprise logging a laser treatment history associated with the patient.

12. The medical device apparatus of claim 9, wherein the acts further comprise tracking a laser calibration history associated with the patient.

13. The medical device apparatus of claim 9, wherein the acts further comprise tracking patient progress associated with the patient.

14. The medical device apparatus of claim 9, wherein the acts further comprise identifying a severity of spinal cord injury and calibrating the laser according to the severity of spinal cord injury.

15. A medical device apparatus, comprising:
a laser configured to emit a laser beam;
a memory having computer executable instructions stored thereon; and a processor communicatively coupled to the memory, the processor executing the computer executable instructions to perform acts comprising:
receiving from a medical professional a neurological level of a patient's spinal cord injury and a neuron activation type;
calibrating the laser to activate neurons in an area proximate to the neurological level and at one or more application angles of the laser beam according to the neuron type to be activated; and
interfacing the medical device apparatus with at least one external entity to transmit a communication to the medical professional to perform a deliberate tactile stimulation on a dermatome corresponding to the neurological level of the patient's spinal cord injury.

16. The medical device apparatus of claim 15, wherein the acts further comprise perform the deliberate tactile stimulation on the dermatome corresponding to the neurological level of the spinal cord injury while activating the neuron type.

17. The medical device apparatus of claim 16, wherein the communication identifies a type of deliberate tactile stimulation, the type of deliberate tactile stimulation being at least one of a deliberate pain stimulation, a deliberate vibration stimulation, a deliberate temperature stimulation, or a deliberate light touch stimulation.

18. The medical device apparatus of claim 15, wherein the acts further comprise logging at least one of a laser treatment history, a laser calibration history, and patient progress associated with the patient.

19. The medical device apparatus of claim 15, wherein the communication identifies a particular application angle of the laser, and wherein varying the particular application angle causes a desired neuron type to be activated more than a different neuron type.

20. The medical device apparatus of claim 19, wherein the particular application angle is an anterior angle when the desired neuron type is a motor neuron, and wherein the particular application angle is a posterior angle when the desired neuron type is a sensory neuron.

* * * * *